United States Patent [19]

Taylor

[11] Patent Number: 5,355,683
[45] Date of Patent: Oct. 18, 1994

[54] CRYOGENIC TEMPERATURE CONTROL AND TENSION/COMPRESSION ATTACHMENT STAGE FOR AN ELECTRON MICROSCOPE

[75] Inventor: Dale E. Taylor, Spotsylvania, Va.

[73] Assignee: The United States of America as represented by the Secretary of the Navy, Washington, D.C.

[21] Appl. No.: 169,922

[22] Filed: Dec. 14, 1993

[51] Int. Cl.⁵ .......................... G01N 3/02; G01N 3/18
[52] U.S. Cl. .................................. 62/51.1; 62/259.1; 62/331; 73/856; 250/443.1; 374/50
[58] Field of Search .................. 62/51.1, 259.1, 295, 62/297, 331, DIG. 10; 73/818, 826, 856, 860; 250/311, 440.11, 443.1; 374/46, 50; 378/79, 80

[56] References Cited

U.S. PATENT DOCUMENTS

| | | | |
|---|---|---|---|
| 2,942,455 | 6/1960 | Smith | 374/50 |
| 3,078,708 | 2/1963 | McClintock | 374/50 |
| 3,212,320 | 10/1965 | McClintock | 374/50 |
| 4,018,080 | 4/1977 | Fletcher et al. | 374/50 |
| 4,346,754 | 8/1982 | Imig et al. | 374/46 |
| 4,408,464 | 10/1983 | Salour et al. | 62/51.1 |
| 4,591,722 | 5/1986 | Biddlecombe et al. | 250/443.1 |
| 4,636,090 | 1/1987 | Baricevac et al. | 374/50 X |
| 4,663,944 | 5/1987 | Bernius et al. | 62/51.1 |
| 4,762,424 | 8/1988 | Baricevac et al. | 73/856 X |
| 4,869,112 | 9/1989 | Gram et al. | 73/856 |

FOREIGN PATENT DOCUMENTS

| | | | |
|---|---|---|---|
| 0796716 | 1/1981 | U.S.S.R. | 374/50 |
| 0855429 | 8/1981 | U.S.S.R. | 374/50 |

*Primary Examiner*—Henry A. Bennet
*Assistant Examiner*—Christopher Kilner
*Attorney, Agent, or Firm*—John D. Lewis; Jacob Shuster

[57] ABSTRACT

A tension-compression attachment stage for an electron microscope having a cryogenic heat exchanger is provided. The attachment stage has a support assembly for mounting brackets to support a pair of load screws and a load screw drive assembly and for mounting a fixed jaw. A moveable jaw is supported and moved by the pair of load screws. A cryogenic heat exchanger is soldered to the fixed jaw and slideably engages the moveable jaw through heat conducting slider blocks. The combination allows control of test specimen test within 1°–4°F.

11 Claims, 2 Drawing Sheets

CRYOGENIC TEMPERATURE CONTROL AND TENSION/COMPRESSION ATTACHMENT STAGE FOR AN ELECTRON MICROSCOPE

ORIGIN OF THE INVENTION

The invention described herein was made in the performance of official duties by an employee of the Department of the Navy and may be manufactured, used, licensed by or for the Government for any governmental purpose without payment of any royalties thereon.

FIELD OF THE INVENTION

The invention relates to the field of material testing and in particular to the stress and strain testing of material while controlling material temperature.

BACKGROUND OF THE INVENTION

In the development and testing of materials, it is often necessary to examine the crystalline structure of a particular material while applying tensile or compression loads. Due to the ability to disclose the structure of space lattices, particularly in alloys and composites, the electron microscope is extensively used. It is known in the field to apply both tensile and compression loads to electron microscope specimens using commercially available attachments. A continuing need within the field includes the ability to maintain a test specimen at a precise temperature during the application of tensile or compression loads. The relatively small size of a typical specimen allows it to rapidly respond to environmental temperature, i.e., the attachment fixture or other surrounding temperatures. As a result, precise temperature is very difficult using present environmental conditioning systems or methods. Further, as the electron microscope emitter must be within the vacuum chamber and direct, near view of the test specimen, only a narrow range of temperatures can be accommodated without interfering with the operation of the electron microscope. More precise temperature control by cooling a test specimen by direct contact with a heat exchanger has been unsatisfactory due to interference with the precision of the test load.

SUMMARY OF THE INVENTION

It is an object of the invention to provide a tension/compression attachment stage for an electron microscope having a cryogenic cooling mechanism incorporated in the attachment clamping jaws.

It is a further object of the invention to provide a cryogenic cooling mechanism which provides a zero force load on the attachment clamping jaws.

It is yet another object of the invention to provide a cryogenic mechanism having a precision temperature control capability.

The invention is an electron microscope tension/compression stage having a cryogenic heat exchanger attached to a stationary jaw on the attachment stage. The attachment stage comprises a base fixture having a load adjustment drive geared to two jaw screws. The jaw screws engage the moveable jaw allowing tensile and compression loads to be applied to a test specimen. The stationary jaw has a cryogenic heat transfer tube molded around and soldered to the jaw perimeter. The moving jaw has a slidable heat transfer block affixed to each end of the moveable jaw. The cryogenic heat transfer tube passes through these heat transfer blocks to provide additional temperature control. During operation of the attachment stage, a cryogenic liquid, such as liquid nitrogen, is pumped through the heat transfer tube, thereby controlling the temperature of both the fixed and moveable jaws.

BRIEF DESCRIPTION OF THE DRAWINGS

The foregoing objects and other advantages of the present invention will be more fully understood from the following detailed description and reference to the appended drawings wherein.

DETAILED DESCRIPTION OF THE INVENTION

Figure 1:
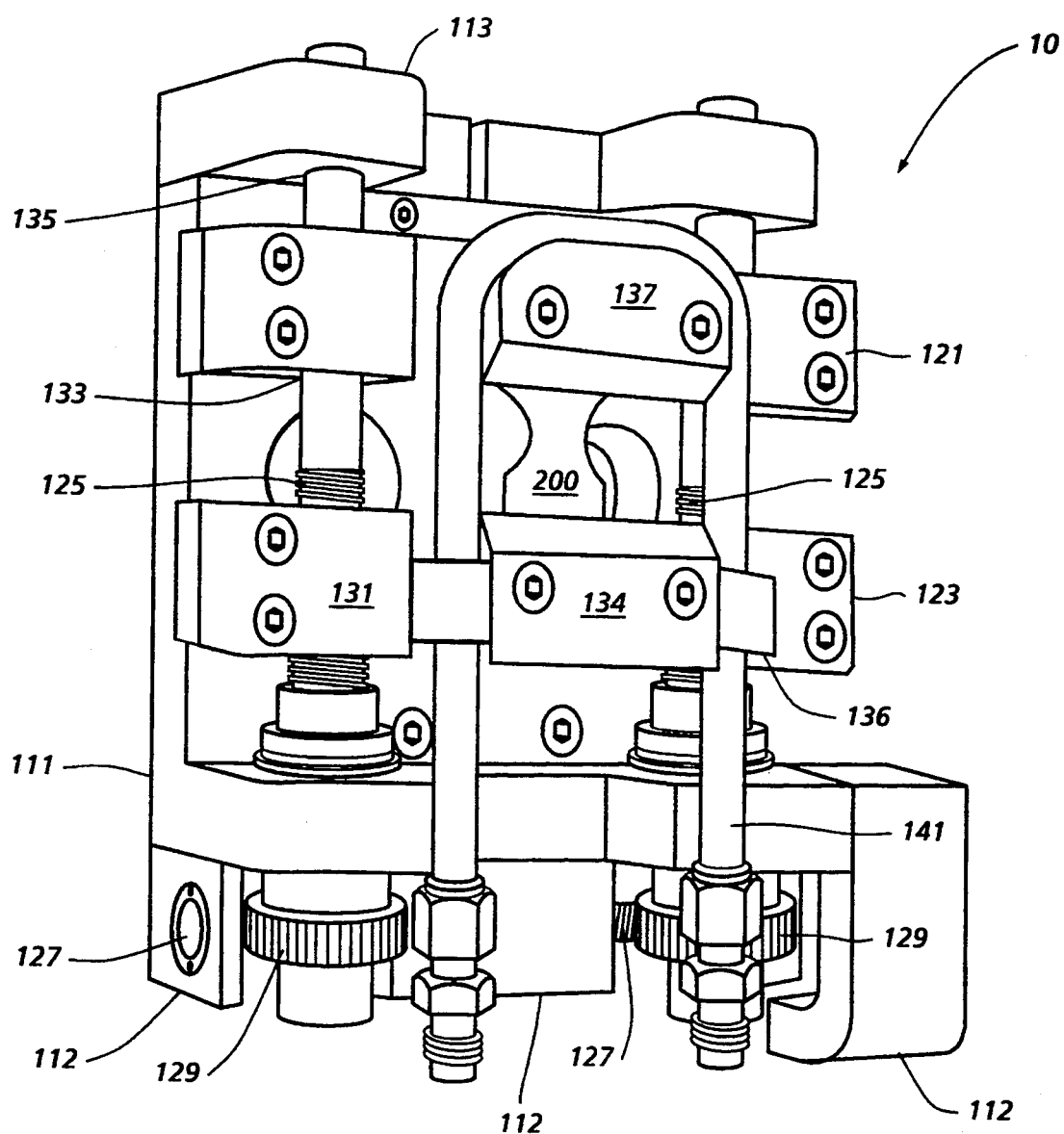
FIG. 1 is a perspective view of the tension-compression attachment stage of the present invention.

Referring now to FIG. 1, the overall tension-compression attachment stage, designated generally by the reference numeral 10, is shown with its major components. The tension-compression attachment stage comprises a base fixture 111 having a drive support bracket 112 attached to its lower surface and a load screw support bracket 113 attached to its upper surface. A fixed jaw assembly 121 is attached to the front face of the base fixture 111. A moveable jaw assembly 123 is mounted on two load screws 125. The load screws 125 are attached to base fixture 111 on bearings having an axial-load carrying design. In the preferred embodiment, a set of ball bearings in raceways are secured to the base fixture by upper and lower retainer rings, thereby allowing both tension and compression loads to be applied to test specimen 200. The load screws 125 are driven by a drive assembly comprising a load adjustment worm drive 127 which extends across the rear portion of drive support bracket 112 and engages screw gears 129. One end (not shown) of the drive assembly accepts a conventional square driver to rotate the worm drive. Moveable jaw assembly 123 has threaded side supports 131 which engage the load screws 125. Load screws 125 pass through fixed jaw 121 via bored holes 134 and are further secured by cylindrical insert bearings 136 in load screw support bracket 113.

The moveable jaw assembly 123 further comprises a moveable jaw 133 which is secured to side supports 131 by slider blocks 135. Slider blocks 135 are bored to slideably engage the cryogenic cooling loop 141. Cryogenic cooling loop 141 also engages the fixed jaw 137.

Figure 2:
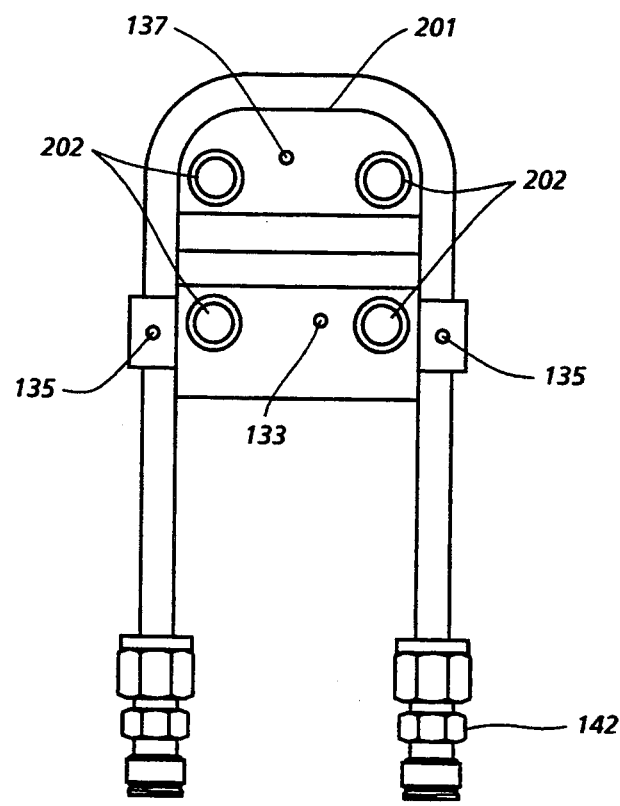
FIG. 2 is a front view of the clamping jaws of the tension-compression attachment stage.

Referring now to FIG. 2, the jaw and cooling loop assembly is shown. The cooling loop 141, having ¼ swage lock connectors 142, is routed around and engages both fixed jaw 137 and moveable jaw 133. A fixed attachment of cooling loop 141 to fixed jaw 137 is made by silver soldering 201 around the outer edge of the fixed jaw. This connection provides support for the cooling loop and excellent heat transfer characteristics. In the preferred embodiment, the cooling loop is a ¼ copper tube. Heat transfer to the moveable jaw 133 is accomplished through slider blocks 135 which are also preferably fabricated using copper. Also shown are bolts 202 used for clamping the jaws of the specimen.

Figure 3:
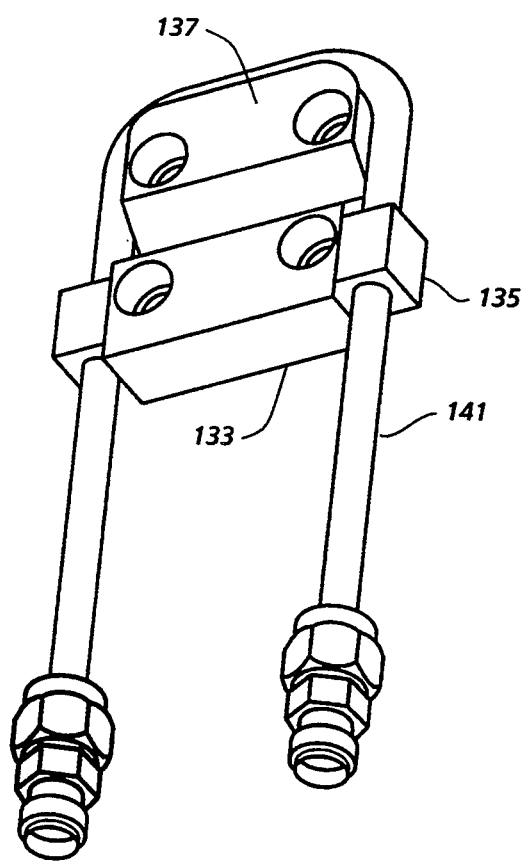
FIG. 3 is a perspective view of the clamps jaws.

FIG. 3 showing the cooling tube-jaw assembly from an upward looking perspective depicts the cooling tube 141 contact with the lower moveable jaw 133. Cooling tube 141 is offset from the center of the slider block 135 so that the cooling tube is in physical contact with the edge of moveable jaw 133. As liquid nitrogen, or other coolant, is pumped through cooling tube 141, heat exchange between the lower moveable jaw 133 is accomplished by conduction through the slider blocks 135 and through direct contact with cooling tube 141. The fixed jaw 137, having a longer contact surface with cooling loop 141 does not require the extra surface as provided on the lower moveable jaw by sliding blocks 135.

Although the invention has been described relative to a specific embodiment thereof, there are numerous variations and modifications that will be readily apparent to those skilled in the art in the light of the above teachings. It is therefore to be understood that, within the scope of the appended claims, the invention may be practiced other than as specifically described.

What is claimed as new and desired to be secured by Letters Patent of the United States is:

1. A tension-compression attachment stage for use with an electron microscope comprising:
   a base fixture having an upper surface, a lower surface, and a front face;
   a drive support bracket attached to the lower surface of said base fixture;
   a load-screw support bracket attached to the upper surface of said base fixture;
   a pair of load screws rotatably mounted in said base fixture and further secured by rotatable mounts in the load screw support bracket;
   a fixed jaw assembly fixed to the front face of said base fixture;
   a moveable jaw assembly mounted on said load screws;
   a drive assembly mounted on said drive support bracket and engaging said load screws and rotatably driving said load screws; and
   a cryogenic cooling loop fixedly mounted on said fixed jaw assembly and slideably mounted on said moving jaw assembly.

2. A tension-compression attachment stage as in claim 1 wherein said pair of load screws are rotatably mounted in said base fixture by axial load carrying bearings.

3. A tension-compression attachment stage as in claim 1 wherein said pair of load screws are rotatably mounted in said load screw support bracket by insert bearings.

4. A tension-compression attachment stage as in claim 1 wherein said fixed jaw assembly further comprises a first jaw attached to said base fixture, said first jaw having holes for pass through of said load screws, and a second jaw screwed to said first jaw, the two jaws providing a gripping mechanism for a test sample.

5. A tension-compression attachment stage as in claim 1 wherein said moveable jaw assembly comprises a first jaw having threaded side supports, each attached to heat conducting slider blocks, which blocks slideably engage said cryogenic cooling loops and provide support for a second moveable jaw.

6. A tension-compression attachment stage as in claim 5 wherein said slider blocks are fabricated using copper.

7. A tension-compression attachment stage as in claim 1 wherein said drive assembly comprises a worm drive engaging the drive gears on said load screws.

8. A tension-compression attachment stage as in claim 1 wherein said cryogenic cooling loop comprises a copper tube soldered to said fixed jaw assembly and slideably engaging said moveable jaws assembly.

9. A tension-compression attachment stage as in claim 8 wherein said copper tube directly and slideably engages the moveable jaw.

10. A tension-compression attachment stage as in claim 1 wherein said fixed jaw assembly comprises a stainless steel jaw.

11. A tension-compression attachment stage as in claim 1 wherein said moveable jaw assembly comprises a stainless steel jaw.

* * * * *